US00PP28787P3

(12) United States Plant Patent
Madsen

(10) Patent No.: US PP28,787 P3
(45) Date of Patent: Dec. 19, 2017

(54) ***SCHLUMBERGERA* PLANT NAMED 'PKMSCHL06'**

(50) Latin Name: ***Schlumbergera truncata* (Haworth) Moran hybr.**
Varietal Denomination: PKMSchl06

(71) Applicant: Gartneriet PKM A/S, Odense N (DK)

(72) Inventor: Christian Hald Madsen, Korsør (DK)

(73) Assignee: Gartneriet PKM A/S, Odense N (DK)

( * ) Notice: Subject to any disclaimer, the term of this patent is extended or adjusted under 35 U.S.C. 154(b) by 88 days.

(21) Appl. No.: 14/998,749

(22) Filed: Feb. 10, 2016

(65) Prior Publication Data

US 2017/0231142 P1 Aug. 10, 2017

(51) Int. Cl.
*A01H 5/02* (2006.01)

(52) U.S. Cl.
USPC ..... Plt./372

(58) Field of Classification Search
USPC ..... Plt./372
See application file for complete search history.

(56) References Cited

PUBLICATIONS

UPOV hit on *Schlumbergera* plant named 'PKMSchL06', QZ PBR 2016/0002, filed Jan. 4, 2016.*
Printout of application information from CPVO Database for corresponding CPVO application No. 2016/0002 filed Jan. 4, 2016 (1 page) (https://cpvoextranet.cpvo.europa.eu).

* cited by examiner

*Primary Examiner* — Anne Grunberg
(74) *Attorney, Agent, or Firm* — Foley & Lardner LLP

(57) ABSTRACT

A new and distinct cultivar of *Schlumbergera truncata* hybr. plant named 'PKMSchl06', characterized by its white and red-purple colored flowers, quick time to flower after short day treatments, and high number of flowers and phylloclades per plant. The claimed variety is particularly suited for production in small (~5.5 cm) pots.

3 Drawing Sheets

Latin name of the genus and species claimed: *Schlumbergera truncata* (Haworth) Moran hybr.
Variety denomination: 'PKMSchl06'.

BACKGROUND OF THE INVENTION

The present invention relates to a new and distinct cultivar of *Schlumbergera* plant, botanically known as *Schlumbergera truncata* (Haworth) Moran hybr., common name Christmas Cactus, and hereinafter referred to by the variety denomination 'PKMSchl06'.

The new *Schlumbergera* is a product of a planned breeding program conducted by the inventor in Søhus, Denmark. The new *Schlumbergera* originated from a crossing made in 2009 by the Inventor between two proprietary, unnamed cultivars of *Schlumbergera truncata* hybr. The Inventor selected the new *Schlumbergera* cultivar from the progeny of the above crossing in 2011 on the basis of its flower color and compact, freely branching habit. Plants of the new *Schlumbergera* are more upright and compact than comparison cultivars.

Asexual reproduction of the new cultivar by phylloclade cuttings taken and propagated and trial production batches in Søhus, Denmark, has shown that the unique features of this new *Schlumbergera* are stable and reproduce true to type in many successive generations.

BRIEF DESCRIPTION OF THE INVENTION

The following traits have been repeatedly observed and are determined to be the unique characteristics of 'PKMSchl06'. These characteristics in combination distinguish 'PKMSchl06' as a new and distinct cultivar:

1. Fast time to flower after end of short day treatments; and
2. Higher number of flowers and phylloclades per plant.
3. Especially suited for production in small (5.5 cm) pots Plants of the cultivar 'PKMSchl06' can be compared to plants of the *Schlumbergera truncata* (Haworth) Moran hybr. cultivar 'PKMSchl05' (U.S. Plant Pat. No. 27,152). However, in side-by-side comparisons conducted over several seasons by the inventor in Søhus, Denmark, plants of the cultivar 'PKMSchl06' and the cultivar 'PKMSchl05' differ in the following characteristics:

1. In plants of the new *Schlumbergera* 'PKMSchl06', the stigma is often protruding from the bud before anthesis which is not the case for the cultivar 'PKMSchl05'.
2. Plants of the new *Schlumbergera* 'PKMSchl06' are more upright than plants of the cultivar 'PKMSchl05'.
3. Plants of the new *Schlumbergera* 'PKMSchl06' flower earlier than plants of the cultivar 'PKMSchl05'.
4. Plants of the new *Schlumbergera* 'PKMSchl06' are more suited for production in small (5.5 cm) pots than plants of the cultivar 'PKMSchl05'.
5. Plants of the new *Schlumbergera* 'PKMSchl06' have smaller phylloclades, buds and flowers than plants of the cultivar 'PKMSchl05'.
6. Plants of the new *Schlumbergera* 'PKMSchl06' have flatter phylloclades than plants of the cultivar 'PKMSchl05'

Data on the parent varieties is no longer available for comparison to the claimed variety.

BRIEF DESCRIPTION OF THE DRAWINGS

The accompanying colored photographs illustrate the overall appearance and details of flower form color and structures of the new cultivar, showing the colors as true as it is reasonably possible to obtain in colored reproductions of this type. Colors in the photographs may differ slightly from the color values cited in the detailed botanical description, which accurately describe the actual colors of the claimed variety. Plants in the photos are approximately 10 months old after start of propagation.

DETAILED BOTANICAL DESCRIPTION

Figure 1:
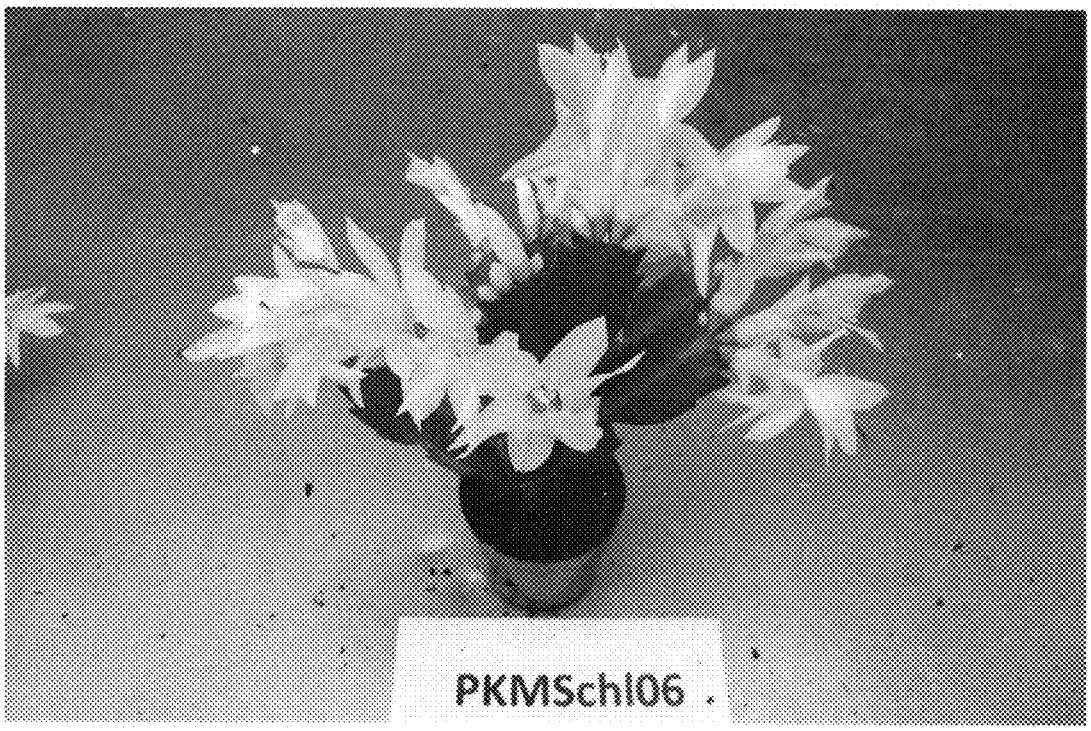
FIG. 1—shows a typical plant of 'PKMSchl06' as grown in a 5.5 cm pot.
Figure 2:
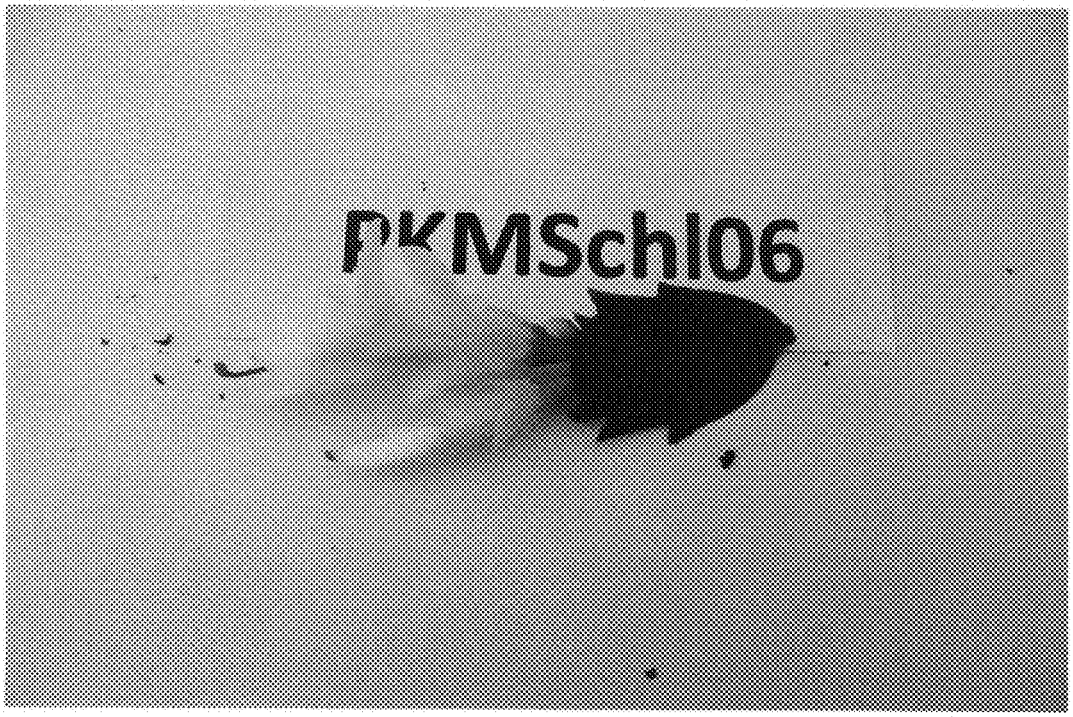
FIG. 2—shows a typical flower, bud and phylloclade of 'PKMSchl06'.
Figure 3:
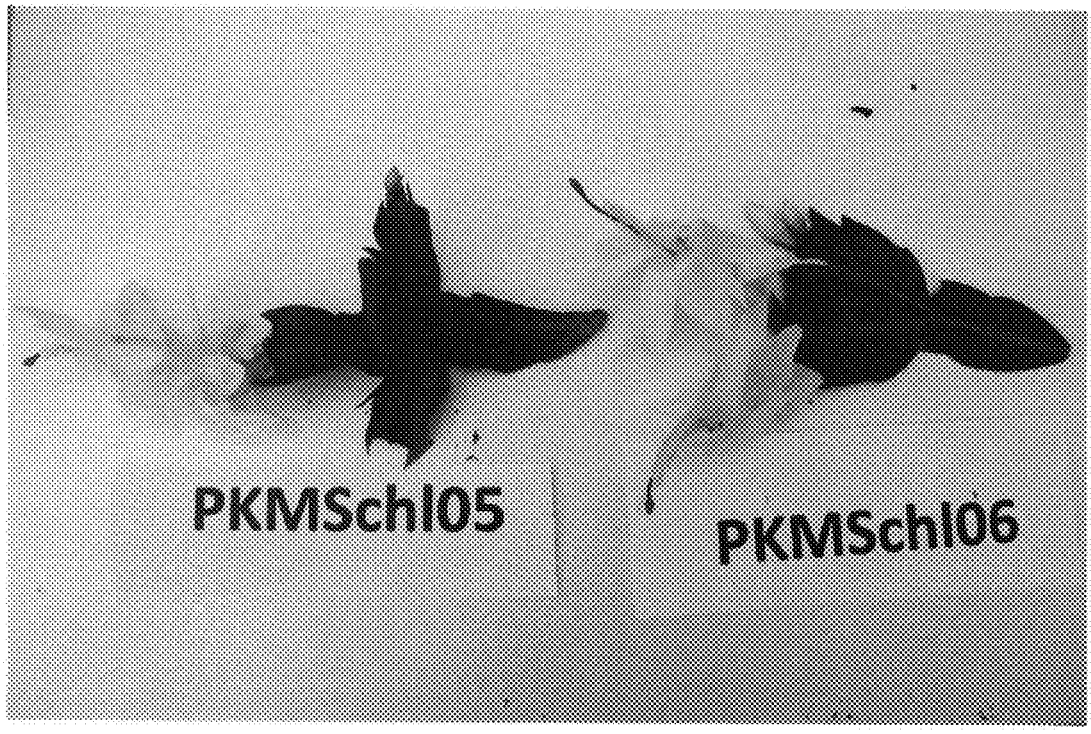
FIG. 3—shows a typical flower and phylloclade of 'PKMSchl06' in comparison with a typical flower and phylloclade of 'PKMSchl05'.

Plants of the cultivar 'PKMSchl06' have not been observed under all possible environmental conditions. The phenotype may vary somewhat with variations in environment such as temperature, light intensity, day length, and fertility level without, however, any variance in genotype.

In the following description, color references are made to The Royal Horticultural Society Colour Chart, 5$^{th}$ edition, where general terms of ordinary dictionary significance are used. Plants were grown under greenhouse conditions. Plants used for this description are about 12 months old.

Classification:

*Botanical.*—*Schlumbergera truncata* (Haworth) Moran hybr.

*Variety denomination.*—'PKMSchl06'.

Parentage:

*Female or seed parent.*—Unpatented, proprietary selection of *Schlumbergera truncata* (Haworth) Moran hybr. (No longer available for comparison.)

*Male or pollen parent.*—Unpatented, proprietary selection of *Schlumbergera truncata* (Haworth) Moran hybr. (No longer available for comparison.)

Propagation:

*Type cutting.*—Single mature phylloclades.

*Form.*—Perennial plant (epiphyte), plants have an upright shape and branched growth habit. Older plants will have more pendulous branches. Flowers singular, double, or triple at apical ends of terminal phylloclades. Freely branching with one to four new phylloclades forming at the apical ends of older phylloclades.

*Crop time.*—After rooting, about 10 months are required to produce finished flowering plants in 5.5 cm pots.

Roots:

*Root initiation.*—2-3 weeks at 21° C.

*Rooting habit.*—Fibrous and well-branched.

*Root color.*—Whitish, older roots can be straw-colored.

Plant:

*Plant height (soil level to top of plant, 2 levels of phylloclades, excl. flowers).*—8.5 cm.

*Vigor.*—Good.

*Growth rate.*—Slow.

*Plant spread.*—10-12 cm.

*Lateral branch length: (2 levels of phylloclades).*—7.5 cm.

Phylloclades:

*Quantity per lateral branch.*—3-5 (2 levels of phylloclades).

*Length.*—3.5-4 cm.

*Width.*—2.3-2.8 cm.

*Thickness.*—Approx. 2 mm.

*Shape.*—Obovate.

*Apex.*—Truncate with 2 protruding marginal teeth, 4-5 mm in length.

*Base.*—Rounded.

*Margin.*—Serrate, 4-6 teeth per phylloclade, 3-5 mm in length.

*Texture.*—Glabrous, smooth.

*Pubescence.*—None.

*Color.*—RHS NN137A, Green.

*Venation pattern.*—Costate.

*Venation color.*—Between RHS NN137A and 144C, Yellow-Green.

Inflorescence:

*Blooming season.*—October to December in the Northern hemisphere. Can be changed with short day treatments. Flowers appear 8-9 weeks after end of short day treatment.

*Longevity on plant.*—Highly dependent on temperature and light conditions; generally 5 to 6 days. Flowers are persistent.

*Buds.*—Aspect: Upright to outward. Length: Up to 2.8 cm before unfolding of tepals (without ovary. Diameter: Up to 1 cm before unfolding of tepals. Shape: Ovoid to lanceolatoid. Color: RHS 4D, yellow in small (~1 cm) buds; RHS 55C, red at tips and RHS 155D, white at base in larger (~3 cm) buds.

*Flowers.*—Arrangement: 1-3 sessile flowers on apical phylloclades. Shape and form: Zygomorphic; tubular with lobes (tepals) extruding at base and at tube end. Fragrance: None. Tepal Arrangement: Inner whorl of tepals fused to form a tube. Corolla tepals are initially at right angle to tube, later somewhat reflexed. Tepal Number: 10 in fused inner whorl forming the tube; 5-7 more or less free tepals in outer whorl. Tepal Shape: Narrow Ovate. Tepal Apex: Apiculate. Tepal Margin: Entire. Tepal Length: 25-30 mm. Tepal Width: 8 mm. Tube Diameter: 8-10 mm. Flower Diameter: 5-5.5 cm. Tube Depth: 3.5 cm. Flower Depth at anthesis: 6 cm. Flower Depth before senescence: 6 cm. Texture: Silky. Color: When opening, upper side: lobes RHS NN155D, White. When opening, under side: lobes RHS NN155D, White. Fully opened, upper side: lobes RHS NN155D, White. Fully opened, under side: lobes RHS NN155D, White; tube N66C, red-purple. Tepal color fading: No fading.

Reproductive organs:

*Stamen.*—Number: Many, polyandrous, phaneranherous. Shape: Incurved. Some filaments fused to perianth tube (connate). Number: 80-100.

*Anther.*—Shape: Basifixed; ovoid. Color: RHS 11C, yellow. Length: 1-2 mm. Pollen: Plenty; color RHS 11D yellow.

*Filament.*—Length: 5-7 cm. Color: RHS 155D, translucent white.

*Pistil*.—Number: 1. Length: 50 mm. Shape: Slightly curved. Can protrude from the buds before bud opening.

*Stigma*.—Shape: Claw-like. Color: RHS 61B, red-purple.

*Style*.—Color: RHS N66A, red-purple. Length: 60 mm.

*Ovary*.—Shape: obovate. Length: 8-10 mm. Width: 6-8 mm. Color: RHS 144A, yellow green (can have a pinkish hue at the base).

Seeds: None observed.

Weather tolerance: Tolerant to a high temperature of 40° C. and a low temperature of 2° C.

Disease/pest resistance: Not tested.

What is claimed is:

1. A new and distinct cultivar of *Schlumbergera* plant named 'PKMSchl06', as illustrated and described herein.

* * * * *